United States Patent
Roe et al.

(10) Patent No.: US 6,501,002 B1
(45) Date of Patent: Dec. 31, 2002

(54) DISPOSABLE SURFACE WIPE ARTICLE HAVING A WASTE CONTAMINATION SENSOR

(75) Inventors: Donald C. Roe, West Chester, OH (US); Anupama R. Mirle, Liberty Township, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/491,445

(22) Filed: Jan. 26, 2000

Related U.S. Application Data

(63) Continuation-in-part of application No. 09/342,308, filed on Jun. 29, 1999.

(51) Int. Cl.⁷ ............................................. A61F 13/15
(52) U.S. Cl. ..................... 604/362; 604/361; 422/56; 422/58; 422/61; 600/309; 600/310; 600/346; 600/362
(58) Field of Search ................................ 604/361, 362; 435/21; 422/56, 58, 61; 374/162; 600/300, 309, 310, 346, 362

(56) References Cited

U.S. PATENT DOCUMENTS

| | | | | |
|---|---|---|---|---|
| 3,918,433 A | * | 11/1975 | Fuisz .......................... | 128/283 |
| 4,114,621 A | * | 9/1978 | Mims, Jr. .................... | 128/288 |
| 4,559,949 A | * | 12/1985 | Levine ........................ | 128/638 |
| 4,724,204 A | * | 2/1988 | Steinbach et al. ............. | 435/26 |
| 5,181,905 A | * | 1/1993 | Flam ........................... | 602/41 |
| 5,217,444 A | * | 6/1993 | Scoenfeld ..................... | 604/361 |
| 5,468,236 A | | 11/1995 | Everhart et al. .............. | 604/361 |
| 5,856,245 A | * | 1/1999 | Caldwell et al. ............... | 442/76 |
| 5,869,172 A | * | 2/1999 | Caldwell ..................... | 428/306.6 |
| 5,998,156 A | * | 12/1999 | Sugiyama et al. .......... | 435/7.92 |
| 6,040,251 A | * | 3/2000 | Caldwell ..................... | 442/123 |
| 6,083,602 A | * | 7/2000 | Caldwell et al. .............. | 428/77 |
| 6,097,297 A | * | 8/2000 | Fard ........................... | 340/604 |
| 6,175,310 B1 | * | 1/2001 | Gott ........................... | 340/605 |
| 6,180,395 B1 | * | 1/2001 | Skiffington et al. ...... | 435/287.6 |
| 6,203,496 B1 | | 3/2001 | Gael et al. | |

FOREIGN PATENT DOCUMENTS

| | | | | |
|---|---|---|---|---|
| JP | 10-313894 | 12/1998 | ............ | C12Q/1/26 |
| WO | WO 97/03209 A1 | 1/1997 | | |
| WO | WO 98/12997 A1 | 4/1998 | | |
| WO | WO 99/31486 | 6/1999 | .......... | G01N/21/47 |
| WO | WO 00/00233 A1 | 1/2000 | | |

* cited by examiner

Primary Examiner—Aaron J. Lewis
Assistant Examiner—Michael Bogart
(74) Attorney, Agent, or Firm—Ian S. Robinson; Matthew P. Fitzpatrick; Ken K. Patel

(57) ABSTRACT

Disclosed is a disposable surface wipe having a sensor which detects bodily waste contamination on a surface and which provides a signal indicating the presence of such contamination, desirably by detecting a component of the waste normally present in waste excreted by healthy individuals and not a component infrequently present in the waste due to special circumstances related to the health or other transient condition of the excreter. The signal provided by the sensor can be visible to a user of the article, and the article can include a substrate which incorporates the sensor. In a preferred embodiment, the article is a cleaning article which can efficaciously clean bodily waste contamination from a surface.

26 Claims, 5 Drawing Sheets

DISPOSABLE SURFACE WIPE ARTICLE HAVING A WASTE CONTAMINATION SENSOR

This application is a continuation in part, and claims priority under 35 USC §120 to application Ser. No. 09/342,308 filed Jun. 29, 1999.

FIELD OF THE INVENTION

BACKGROUND OF THE INVENTION

Today, disposable surface wipe articles, such as disposable hand wipes, baby wipes, paper towels, facial tissues, toilet tissues and other cleaning articles, are widely used in personal (animate surface) and environmental (inanimate surface) hygiene, such as in the care of infants and incontinent individuals as a means of cleaning (removing) bodily wastes and other contaminants. These articles have generally replaced reusable, washable cloth articles as the preferred means for these applications because of their convenience and reliability.

Conventional disposable surface wipes, such as the cleaning articles listed above, do not provide any indication of the presence of, or the efficacy of removal of, bodily waste contamination which is undetectable by unaided human vision. This is an important limitation due to the potential for skin irritation (in the case, for example, of feces) if waste residue is left on the skin and/or the potential for further spreading waste to other contacted surfaces thereby spreading potentially harmful organisms or other waste components to such surfaces.

Accordingly, it would be advantageous to provide disposable surface wipe articles or gloves that respond to fecal or other bodily waste contamination by detecting and signaling the presence of the contamination to the user of the article.

SUMMARY OF THE INVENTION

The present invention is directed to a disposable surface wipe having a sensor which detects bodily waste contamination on a surface contacted by the article and which provides a signal indicating the presence of such contamination, preferably by detecting a component of the waste normally present in waste excreted by healthy individuals and not a component infrequently present in the waste due to special circumstances related to the health or other transient condition of the excreter.

In one preferred embodiment, the signal provided by the sensor is visible to a user of the article. In another preferred embodiment, the article includes a substrate which incorporates the sensor. In yet another preferred embodiment, the article is a cleaning article that includes a substrate which incorporates the sensor and which is useful for cleaning waste contamination from a surface.

While the specification concludes with claims that particularly point out and distinctly claim the present invention, the following description taken in conjunction with the accompanying drawings describe the invention and preferred embodiments thereof.

DETAILED DESCRIPTION OF THE INVENTION

The present invention is directed to a disposable surface wipe article having a sensor which detects bodily waste contamination on a surface contacted by the article and which provides a signal indicating the presence of such contamination. The term "disposable" is used herein to describe articles which generally are not intended to be laundered or otherwise restored or reused as an absorbent article (i.e., they are intended to be discarded after a single use and, preferably, to be recycled, composted, flushed, or otherwise disposed of in an environmentally compatible manner). The term "surface wipe article" is used herein to describe articles which are intended to be used for wiping either an animate surface such as the human skin, or an inanimate surface such as a floor, wall, furniture, faucet, doorknob or toy surface. For example, disposable surface wipe articles include facial tissues, toilet tissues, paper towels, dry wipes, and wet wipes such as hand wipes or baby wipes.

The disposable surface wipes of the invention preferably include a substrate and a bodily waste contamination sensor or sensing system incorporated into or onto the substrate. A wide variety of substrates can be used in the disposable surface wipe of the present invention. The substrate may be a nonwoven or woven fibrous material, or a nonfibrous material. The material, form, and design will depend upon the type of article and its intended use. By way of example, materials which can be used include fibers, sponges, closed cell foams, open cell foams, latex, rubber, polymeric materials (such as plastics, especially biodegradable plastics). The substrates can be non-absorbent or absorbent, and can contain optional materials such as superabsorbent polymeric gelling materials.

Figure 1:
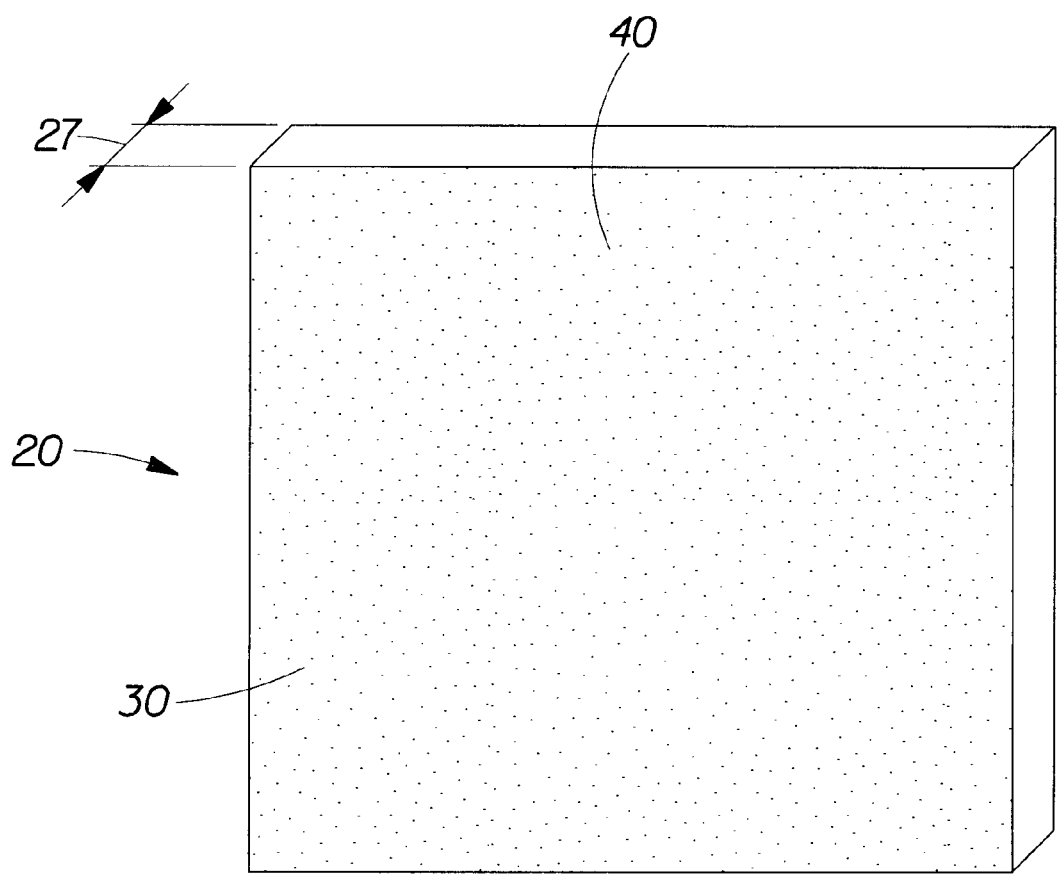
FIG. 1 is a perspective view of a disposable surface wipe article of the invention.

FIG. 1 is a perspective view of an article 20 of the present invention which comprises a substrate 30 suitable for cleaning contaminants from a surface. Article 20 may be, for example a baby wipe suitable for wiping feces and urine from an animate surface such as a baby's skin, or a paper towel or tissue suitable for wiping spills or bodily waste from an inanimate surface such as a wall or furniture. Substrate 30 can be any woven or nonwoven fibrous material, or a non-fibrous material. Preferably, substrate 30 is a fibrous material such as a cellusosic or synthetic polymeric material such as polyethylene or polypropylene, or a combination thereof. Substrate 30 has thickness 27, which can vary depending upon intended use and materials of construction, but generally will be between about 0.05 cm and about 2 cm, more generally between about 0.1 cm and about 1 cm. Substrate 30 can be of any width and length, and can also be a continuous roll.

Fibrous substrates for use in the invention can include natural fibers, synthetic fibers, or mixtures of natural and synthetic fibers. Suitable natural fibers include but are not limited to cellulosic fibers, such as wood pulp fibers, cotton, hemp, wool, and rayon. Suitable synthetic fibers include fibers commonly used in textiles, including but not limited to polyester and polypropylene fibers.

Various forming methods can be used to form a suitable fibrous substrate, sometimes referred to as a web. For instance, the substrate or web can be made by nonwoven dry forming techniques, such as air-laying, or alternatively by wet laying, such as on a papermaking machine. Other nonwoven manufacturing techniques, including but not limited to techniques such as melt blowing, spunbonding, needle punching, and hydroentanglement methods may also be used.

In one embodiment, the fibrous substrate can be a dry fibrous airlaid nonwoven web comprising a combination of natural fibers, staple length synthetic fibers and a latex binder. The dry fibrous web can, for example, be about 20–80 percent by weight wood pulp fibers, 10–60 percent by weight staple length polyester fibers, and about 10–25 percent by weight binder. The dry fibrous web can, without limitation, have a basis weight of between about 40 and about 80 grams per square meter. The density of the dry fibrous web can be, for example, less than about 0.12 grams per cubic centimeter. As used herein, "density" is the basis weight of the dry fibrous web divided by the thickness of the dry web, measured in consistent units, where the thickness of the dry web is measured using a circular load foot having an area of about 2 square inches and which provides a confining pressure of about 95 grams per square inch. In one embodiment, the dry fibrous web can have a basis weight of about 64 grams per square meter, a thickness of about 0.06 cm, and a density of about 0.11 grams per cubic centimeter.

The dry fibrous web can comprise at least 50 percent by weight wood pulp fibers, and more preferably at least about 70 percent by weight wood pulp fibers. One particular airlaid nonwoven web which is suitable for use in the present invention comprises about 73.5 percent by weight cellulosic fibers (Southern softwood Kraft having an average fiber length of about 2.6 mm); about 10.5 percent by weight polyester fibers having a denier of about 1.35 gram/9000 meter of fiber length and a staple length of about 0.85 inch; and about 16 percent by weight of a binder composition comprising a styrene butadiene copolymer. The binder composition can be made using a latex adhesive commercially available as Rovene 5550 (49 percent solids styrene butadiene) available from Mallard Creek Polymers of Charlotte, N.C.

Another suitable airlaid nonwoven web for use in the present invention is the airlaid nonwoven web employed in PAMPERS BABY FRESH baby wipes marketed by The Procter & Gamble Company of Cincinnati, Ohio. Such a web is disclosed generally in U.S. application Ser. No. 08/915,349 entitled "Disposable Premoistened Wipe Having Opacity Agent", filed Aug. 22, 1997 in the name of Gorely, which application is incorporated herein by reference, and includes about 76.4 percent cellulosic fibers, 12.9 percent polyester fibers, and 10.7 percent adhesive binder.

The following patents are also incorporated herein by reference for their disclosure related to suitable fibrous webs: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; U.S. Pat. No. 4,637,859 issued Jan. 20, 1987; U.S. Pat. No. 5,223,096 issued Jun. 29, 1993; U.S. Pat. No. 5,240,562 issued Aug. 31, 1993; U.S. Pat. No. 5,556,509 issued Sep. 17, 1996; U.S. Pat. No. 5,580,423 issued Dec. 3, 1996; and U.S. Pat. No. 5,840,403 issued Nov. 24, 1998.

The substrate can be single ply or multi-ply, single density or multi-density, and single basis weight or multi-basis weight. Multi-density webs may be made by processes well known in the art. The following patents disclose processes for making webs that can be used in the present invention: U.S. Pat. No. 4,529,480, issued Jul. 16, 1985 to Trokhan; U.S. Pat. No. 4,637,859, issued Jan. 20, 1987 to Trokhan; U.S. Pat. No. 5,364,504, issued Nov. 15, 1994 to Smurkoski et al.; U.S. Pat. No. 5,529,664, issued Jun. 25, 1996 to Trokhan et al.; U.S. Pat. No. 5,679,222 issued Oct. 21, 1997 to Rasch et al.; U.S. Pat. No. 5,714,041 issued Feb. 3, 1998 to Ayers et al.; U.S. Pat. No. 5,906,710, issued May 25, 1999 to Trokhan, all commonly assigned to The Procter & Gamble Co., Cincinnati, Ohio, USA, the disclosures of which are incorporated herein by reference. Multi-basis weight webs and methods for making them are disclosed in U.S. Pat. No. 5,503,715, issued Apr. 2, 1996 to Trokhan et al.; U.S. Pat. No. 5,614,061, issued Mar. 25, 1997 to Phan et al.; U.S. Pat. No. 5,804,281 issued Sep. 8, 1998 to Phan et al.; and U.S. Pat. No. 5,900,122 issued May 4, 1999 to Huston, the disclosures of which are incorporated herein by reference.

The substrate can comprise a hydroentangled web having a basis weight of about 62 grams per square meter and comprising about 50 percent by weight rayon fibers and about 50 percent by weight polyester fibers, polypropylene fibers, or a combination thereof. In still another embodiment, the substrate can comprise a laminate of two outer hydroentangled webs, such as nonwoven webs of polyester fibers having a basis weight of about 30 grams per square meter, joined to an inner constraining layer, which can be in the form of net-like scrim material which contracts upon heating to provide surface texture in the outer layers.

In a number of applications, for example, in situations wherein a liquid-removal function is the primary function to be performed by the surface wipe article, it is preferred that the substrate be substantially free of water or other liquid. Examples of surface wipe articles for these applications include paper towels and facial tissues. In other applications, for example, where removal of non-liquids (such a pasty, semi-solid or solid substances) is also to be performed, it may be preferable to incorporate water or other liquids into the substrate. Examples of surface wipe articles for these applications include baby wipes, hand wipes, hard surface cleansing wipes, and other so-called "wet wipes". In these cases, the substrate can be premoistened, for example, with an emollient, lotion, tonic, disinfecting liquid, sanitizing liquid, cleansing liquid, or other liquid suitable for application to an object intended to be wiped. The liquid can be water, another aqueous fluid, or hydrophilic liquids (such as ethanol), or lipdphilic liquids (such as silicones, hydrocarbons, or oils), and combinations thereof. Premoistened wipes can be made by wetting the dry substrate with, preferably, at least 1 gram of premoistening liquid per gram of dry fibrous web. Preferably, the dry substrate is wetted with at least about 2.0, and more preferably at least about 2.5 grams of liquid per gram of the dry fibrous web.

The liquid used for premoistening the wipe substrate can be a lotion comprising a water soluble silicon based surfactant, for example, an anionic silicon based sulfosuccinate surfactant. Suitable counter ions include those derived from the alkaline metals (e.g. sodium, potassium); the alkaline earth metals (e.g. magnesium, calcium); ammonia, and alkanol amines (e.g. mono, di, and tri ethanol amines). The lotion can comprise water and a silicon copolyol sulfosuccinate selected from the group consisting, of disodium dimethicone copolyol sulfosuccinate and diammonium dimethicone copolyol sulfosuccinate. Preferably, the lotion comprises less than about 1.00 percent by weight of the silicone based sulfosuccinate. In particular, the lotion can comprise less than about 0.20 percent by weight of the silicone based sulfosuccinate, and in one embodiment comprises between about 0.08 and about 0.10 percent by weight of the silicone based sulfosuccinate. Preferably, the lotion comprises no more than about 1.00 percent by weight total surfactant solids, including the silicone based sulfosuccinate. A suitable disodium dimethicone copolyol sulfosuccinate is commercially available as MACKANATE DC-30 and MACKANATE DC-50 brand sulfosuccinate surfactants available from the McIntyre Group, LTD, University Park, Ill. A suitable diammonium dimethicone copolyol sulfosuccinate is commercially available as MACKANATE DC-30A from the same supplier. U.S. Pat. No. 4,849,127 issued Jul. 18, 1989 to Maxon is incorporated herein by reference for its disclosure related to dimethicone copolyol sulfosuccinates.

The liquid used to premoisten the wipe substrate can also comprise one or more of the following: an effective amount of a preservative, an effective amount of a humectant, an effective amount of an emollient; an effective amount of a fragrance, and an effective amount of a fragrance solubilizer. As used herein, an emollient is a material that softens, soothes, supples, coats, lubricates, or moisturizes the skin. The term emollient includes, but is not limited to, conventional lipid materials (e.g. fats, waxes), polar lipids (lipids that have been hydrophilically modified to render them more water soluble), silicones, aloe extracts such as aloe vera, hydrocarbons, and other solvent materials. Emollients useful in the present invention can be petroleum based, fatty acid ester type, alkyl ethoxylate type, fatty acid ester ethoxylates, fatty alcohol type, polysiloxane type, mucopolysaccharides, or mixtures thereof. Humectants are hygroscopic materials that function to draw water into the stratum comeum to hydrate the skin. The water may come from the dermis or from the atmosphere. Examples of humectants include glycerin, propylene glycol, and phospholipids. Fragrance components, such as perfumes, include, but are not limited to water insoluble oils, including essential oils. Fragrance solubilizers are components which reduce the tendency of the water insoluble fragrance component to precipitate from the lotion. Examples of fragrance solubilizers include alcohols such as ethanol, isopropanol, benzyl alcohol, and phenoxyethanol; any high HLB (HLB greater than 13) emulsifier, including but not limited to polysorbate; and highly ethoxylated acids and alcohols. Preservatives prevent the growth of micro-organisms in the liquid lotion and/or the substrate. Generally, such preservatives are hydrophobic or hydrophillic organic molecules. Suitable preservatives include, but are not limited to parabens, such as methyl parabens, propyl parabens, and combinations thereof.

The liquid used to premoisten the wipe substrate can also comprise an effective amount of a kerotolytic for providing the function of encouraging healing of the skin. An especially preferred kerotolytic is Allantoin ((2,5-Dioxo-4-Imidazolidinyl)Urea), a heterocyclic organic compound having an empirical formula $C_4H_6N_4O_3$. Allantoin is commercially available from Tri-K Industries of Emerson, New Jersey.

U.S. Pat. No. 5,534,265 issued Jul. 9, 1996; U.S. Pat. No. 5,043,155 issued Aug. 27, 1991; and U.S. Pat. No. 5,648,083 issued Jul. 15, 1997 are incorporated herein by reference for the purpose of disclosing additional ingredients for use in suitable premoistened wipe substrates. U.S. Pat. No. 4,904,524 (Yoh), issued Feb. 27, 1990 and incorporated herein by reference, discloses a baby wipe comprising a suitable substrate impregnated with an aqueous lotion and a hydrophobic functional ingredient (e.g., dimethicone) entrapped in polymeric beads (e.g. microsponges, microcapsules) concentrated near the surface of the substrate. Suitable premoistened wipe substrates can also be made as described in U.S. Pat. No. 4,300,981 (Carstens, issued Nov. 17, 1981); U.S. Pat. No. 4,112,167 (Dake et al., issued Sep. 5, 1978); U.S. Pat. No. 4,481,243 (Allen, issued Nov. 6, 1984); U.S. Pat. No. 4,513,051 (Lavash, issued Apr. 23, 1985); and U.S. application Ser. No. 09/132,883 (Hanser et al., filed Aug. 12, 1998), all hereby incorporated by reference.

A disposable wet wipe having a premoistened substrate suitable for use in the present invention is also available as PAMPERS BABY FRESH from the Procter & Gamble Co. of Cincinnati, Ohio. Such a wipe is described, modified as noted below, in the Example set forth in U.S. application Ser. No. 08/915,349 entitled "Disposable Premoistened Wipe Having Opacity Agent", filed Aug. 22, 1997 in the name of Gorely, which application was earlier incorporated herein by reference. The Example in the aforesaid application is modified to make the PAMPERS BABY FRESH wipe by including about 76.4 percent cellulosic fibers, 12.9 percent polyester fibers, and 10.7 percent adhesive binder (the binder contains no titanium dioxide) in the substrate web. The web is embossed using the pattern described below, with an embossing roll having a land area of about 18 percent. The amount of binder adhesive sprayed on the web is sufficient to provide a dry web having about 10.7 percent by dry weight binder adhesive solids (this dry substrate or web is hereinafter referred to as the PAMPERS BABY FRESH dry substrate). As indicated in the aforesaid Example, a "wet wipe" having premoistened substrate is obtained by moistening the PAMPERS BABY FRESH dry substrate with a liquid composition comprising about 97% water, with the remaining 3% being the other listed minor constituents. The embossing pattern for the PAMPERS BABY FRESH wipe is depicted in U.S. Design Patent No. 400,716, issued Nov. 10, 1998, which is also incorporated herein by reference, the wipe having an embossing pattern repeat of 16.0 cm (6.3 inches), the character line thickness being 0.081 cm (0.032 inches), and the elipses having a major diameter of 0.28 cm (0.11 inches) and minor diameter of 0.14 cm (0.055 inches).

As described above, the disposable surface wipe articles of the present invention may comprise wet or dry substrates. In certain preferred embodiments, the substrate is a wet substrate, containing free liquid water or other aqueous fluid on its surface or held within pores, capillaries, voids, etc. within or on the body of the substrate. Many of the sensors described herein, especially those dependent on chemical or biological reactions, require the presence of water or another aqueous fluid to function properly. The water, or other aqueous fluid, is liberatable from the substrate under normal usage conditions, such as upon contact with a surface or upon application of wiping pressure. The liberated water or other aqueous fluid is then available to enable or facilitate the sensor reaction (such as a chemical reaction to detect the waste contamination or a component thereof) to proceed in the cases where the contamination is substantially anhydrous and contains insufficient "free" or unbound water to enable the reaction, for example as in the case of dried fecal contamination on a baby's skin or on inanimate environmental surfaces. Without the water or other aqueous fluid available from the wet substrate of the article, the sensor could fail to detect waste contamination on the surface of interest. Dry substrates, however, may be appropriate for applications wherein the waste contamination is reasonably expected to contain sufficient water to allow the sensor to function properly, such as in the case of detecting "fresh" faces on baby's skin. In certain embodiments, a wipe substrate may be tactilely dry, but carry its own supply of water, or other aqueous fluid, sufficient to enable the detection reaction. For example, a "dry" wipe may comprise a high internal phase emulsion disposed on a substrate, wherein the emulsion ruptures to release water (alone or with additives such as a disinfectant) when subjected to shear or pressure during the wiping of skin or another surface. Such dry wiping substrates are described more fully in U.S. Pat. Nos. 5,756,112; 5,763,332; 5,863,663; 5,914,177 and 5,948,540 (Mackey et al.), all of which are incorporated herein by reference.

Referring again to FIG. 1, the, disposable surface wipe or cover article 20 includes at least one sensor 40, adapted to detect one or more markers of bodily waste contamination on a surface contacted by the article, and having the capability to provide a signal of such detection to the user or caretaker. Preferably, the sensor 40 is incorporated into or onto a surface-contacting substrate 30. The sensors of the present invention may also be associated with a carrier structure. The carrier structure may hold, stabilize, and/or at least partially encapsulate the sensor. Examples of carrier structures include one or more layers of woven and non-woven webs, films, foams, scrims, hydrogels, sponges, and the like. The sensor may be attached to the carrier structure, held between two or more components, layers, or folds of the carrier structure, or may be sealed within the carrier structure. The carrier structure may be attached to the substrate 30 of the disposable surface wipe article. The sensor, and/or carrier if a carrier is utilized, may additionally comprise an element adapted to retaining the sensor and/or controlling the access of the contamination, or component thereof, to the sensor. For example, a semi-permeable or selectively permeable membrane may be employed to restrict the rate of access of the contaminant to the sensor or to restrict access to the sensor to specific elements, molecules, or organisms (such as specific pH, size, bio-specificity, and so forth). The access control element may additionally comprise a semi-permeable film, as known in the drug delivery and electrodialysis art, for example, or a soluble (such as a water soluble) coating.

As used herein, the term "sensor" refers to a device or system that is capable of detecting an event or a parameter that is associated with an event. For the purposes of this invention, an event may include the contamination of an animate surface (for example, on buttocks, hands, face, or another skin area), or the contamination of an inanimate environmental surface, with bodily waste such as feces (the waste contamination of interest may be referred to as the target contamination or contaminant). A parameter associated with an event is any measurable signal that correlates with the occurrence of an event within the frame of reference of the system (such as a signal caused by the bodily waste or a component thereof). Sensors include anything that responds to one or more specific inputs. Sensors may be chemical, electrochemical, biochemical, or biological, mechanical, magnetic, thermal, or other sensors as are known in the art. The articles of the present invention specifically comprise sensors that provide a signal to a user or caretaker indicating the detection of bodily waste of interest, such as feces, urine, mucous, saliva, sebum, sweat, ejaculates such as semen, or menses, on a surface.

Preferably, the detection signal provided by the sensor 40 is an optical signal, including a signal (such as a colorimetric or flourescent indicator) which is visible to the unaided eye of a user of the surface wipe article (as used herein, the term "user" includes, for example, a caretaker of an individual, such as a baby, on which the wipe article may used). A colorimetric signal is particularly preferred. This colorimetric signal is preferably distinct (for example, a change in color vs. intensity or shade) and rapid, since the disposable surface wipe articles of the present invention typically have extremely short usage periods. The visual indication may include a pattern or other visual indicia such as luminescence. Alternatively, the signal provided by sensor 40 may be a chemical signal (such as a change in pH, enzyme activity, or concentration of any other chemical species), or an electrical signal, which may be processed via an associated transducer which, for example, may produce or amplify an electrical signal (such as a current, potential, inductance, or impedance) that may be displayed (such as on a readout such as an LED or LCD display) or which triggers an audible or tactile (e.g., vibration) signal. The signal may be qualitative (for example, indicating the presence of waste contamination) or quantitative (for example, a measurement of the amount or concentration of the waste contamination).

In certain preferred embodiments, the signal from sensor 40 is available to the user prior to the completion of any detection reaction process. The time between the beginning of use by a user and the time at which the disposable wipe article is discarded is typically less than about 30 seconds and may be considerably shorter. For any signal of contamination to be useful, the signal must be detectable by a user during the useful life of the article. It is therefore evident that, considering the relatively short useful life of articles of the present invention (compared, for example, with disposable diapers), response speed is critical. Preferably, the signal is provided within less than about 30 seconds of the time the article contacts the, target waste contamination. More preferably, the signal is provided within less than about 15 seconds of the time of contacting the target contamination. Even more preferably, the signal is provided within less than about 10 seconds of the time of contacting the target contamination. Most preferably the signal is provided within less than about 5 seconds of the time of contacting the target contamination.

In any case, the signal provided by sensor 40 may be durable (stable and readable over a length of time typically at least of the same magnitude as the usage life of the article) or transient (registering a real-time measurement). Since the useful life of the disposable wipe articles of the present invention is typically short, however, there is no need for a stable visual endpoint or indication. Once the article is discarded, loss of the signal is irrelevant. Further, the sensor 40, or any of its components, may be adapted to detect and/or signal only concentrations of the waste contamination above a predefined threshold level (such as in cases wherein the contamination level is below typical background levels). Regardless of the type of disposable surface wipe article, the signal is preferably generated and/or displayed on the article or another operatively connected component as described herein, and not on the contaminated surface itself.

Significantly, the present invention is primarily directed to the detection of any waste contamination by detecting a component of the waste normally present in the waste excreted by healthy individuals (in other words, the component is something expected in all typical waste samples) and not a component infrequently present in the waste due to special circumstances related to the health or other transient condition of the excreter. It is important, for instance, in the case of feces remaining on an animate surface such as a baby's skin, to be able to detect such a condition and remediate it in order to prevent skin irritation and/or accidental spread of the contamination, which may contain pathogens or other potentially harmful substances, to inanimate surfaces such as toys, changing tables, and the like. It is also important, for example, in the case of feces which may have contaminated an inanimate surface, to be able to detect such a condition and remediate it in order to prevent accidental spread of the; contamination from the surface to humans.

The presence of bodily waste contamination on a surface may be observed by detecting a normally occurring component of the waste as a marker. For example, the marker may comprise any elemental, chemical, or biological components that may be normally found in the contaminating waste of interest. The markers may comprise, for example, enzymes from endogenous or microbial origin such as trypsin, chymotrypsin, amylase, elastase, lipase, leucine aminopeptidase, and acid or alkaline phosphatase, among others. The marker may also comprise one or more bacteria such as Bifidobacteria and Lactobacillus. These enzymes and bacteria are, for example, commonly found in the feces of healthy babies. Other suitable markers may include mucous and other endogenous secretions (e.g., bile acids and salts thereof), proteinaceous material, fats (e.g., free fatty acids such as myristic, linoleic, palmitic, stearic, and oleic acids), soaps (e.g., palmitic and stearic acid soaps), electrolytes (e.g., aluminum, calcium, chlorine, copper, tin, zinc, sodium, iron, magnesium, manganese, phosphorous, sulphur, bicarbonate, and potassium), vitamins and related compounds (e.g., thiamine, riboflavin, niacin, biotin, pantothenic acid, folic acid,: ascorbic acid, and vitamin E), amino acids and other nitrogenous compounds (e.g., histidine, arginine, isoleucine, leucine, lysine, threonine, valine, etc.), carbohydrates, and other organic materials (e.g., long chain alcohols, long chain esters, triglycerides, hydrocarbons).

An exemplary sensor (sensing system) is based on the detection of alkaline phosphatase (ALP) in fecal contamination., ALP has been found to be present in the feces of babies from shortly after birth to at least the onset of toilet training. This exemplary sensor is prepared as follows. A buffer solution is prepared by mixing 3.14 grams of sodium carbonate (anhydrous) in 500 ml deionized water, followed by the addition of 9.5 grams of Borax, available as catalog #22133-3 from Sigma-Aldrich of St. Louis, Miss. The buffer solution is then stirred until the solids are dissolved. A cofactor solution is also prepared by dissolving 0.203 grams of magnesium chloride in 500 ml of deionized water. An indicator solution is prepared by dissolving 1.00 grams of phenolphthalein diphosphate in 200 ml of the buffer solution, and subsequently adding 1.0 ml of the cofactor solution to this mixture. A 0.133% (w/V) Nile Blue Chloride solution is prepared by dissolving 34.4 micrograms of solid Nile blue chloride, available from Sigma-Aldrich, in 25 ml of isopropanol. A detecting solution (i.e., sensor system) is prepared by adding 1.0 ml of the 0.133% (w/V) Nile Blue Chloride solution to 25 ml of the indicating solution. The detecting solution is applied by spraying the detecting solution using a 50 ml tube-type sprayer available as Z12-629-2, available from Sigma-Aldrich, onto the previously mentioned PAMPERS BABY FRESH dry substrate and allowing the web to dry. The detecting solution is applied to the substrate at a basis weight of 0.038 g/cm$^2$ (6 ml of the detecting solution sprayed evenly over a 8.9 cm by 17.8 cm substrate) and allowed to dry. Upon contact with residual fecal contamination, ALP in the feces cleaves the phosphate groups from the phenolphthalein diphosphate, resulting in a pink visual signal from the phenolphthalein within 5 seconds or less.

In certain preferred embodiments of the foregoing example, the range of concentration of ALP in the detecting solution is from about 0.1% to about 10% (wNV). However, concentrations outside this range are contemplated, including the application of neat phenolphthalein diphosphate to the substrate. In addition, in preferred embodiments of the foregoing the example, the color of the PAMPERS BABY FRESH dry substrate used is white. However, the substrate color may be varied to moderate or change the color of the signal (such as a blue substrate to turn the signal into more of a purple color). Further, the substrate may alternatively be any fibrous web, such as the fibrous webs typically found in toilet tissue, facial tissue, paper towels, and other cleaning wipes. Such substrates, in combination with the above-described sensor, can be used to form a disposable wipe article of the present invention.

A surface wipe article of the present invention, similar to the foregoing example but having a wet substrate, may be prepared by spraying 10 ml of phenolphthalein diphosphate in a solution at approximately pH=8.5 evenly on the PAMPERS BABY FRESH premoistened wipe previously described herein. Additionally, phenolphthalein diphosphate, an aqueous solution thereof, or an alternate sensor, may be microencapsulated via the approach described in U.S. Pat. Nos. 5,756,112; 5,763,332; 5,863,663; 5,914,177 and 5,948,540 (Mackey et al.), all of which were earlier incorporated herein by reference.

Other indicating solutions may also be prepared based on detecting any of the potential contamination markers described herein. For example, detection of fecal contamination may also be accomplished using p-nitrophenol in a detecting solution. Additionally, substances such as chitosan may be added to the detecting solutions to increase their binding to the substrate and reduce the potential transfer of the solution to the contaminated surface.

In instances where the article includes a substrate which comprises its own supply of water or other aqueous fluid, the sensor 40 may detect abnormal health and/or nutritional markers in bodily waste excreted by an individual, and to signal the presence of the abnormality to a user of the article. Suitable signals, and preferred attributes of such signals, are discussed above and further below in connection with the sensors of the invention. In this case, since the substrate provides the water required for the detection reaction, the reaction conditions may be :better controlled so as to enable more reliable detection of small variations in waste components indicative of abnormal conditions. "Health markers" and "nutritional markers" (for example, in human feces or mucous), as used herein, refer to any elemental, chemical, or biological components that may be found in the waste, and any combinations of, or relationships (such as ratios) between the components, having a defined relationship with the human health (such as disease, infection, poisoning) and nutritional status, respectively. The nutritional status of an individual includes, for example, metabolic efficiency, nutrient deficiencies, nutrient absorption or malabsorption, food and drink intake, food allergies (e.g., to peanuts), food intolerance (e.g., lactose intolerance), colonic bacteria ecology (e.g., beneficial bacteria such as bifidobacteria and lactobacillus), and total energy balance. Health markers may include heavy metals (e.g., lead, mercury, etc.), radioactive substances (e.g., cesium, strontium, uranium, etc.), fats, enzymes, endogenous secretions, proteinaceous matter (e.g., casts), mucous, and microorganisms (described in more detail hereinafter in the biosensor section) that may be related to various health issues such as skin irritation, infection, diarrhea, gastrointestinal distress or disease, or poisoning. Proteinaceous masses, such as casts (e.g., in urine) may be sensed by targeting Tamm-Horsfall protein. A suitable example of a sensor for Tamm-Horsfall protein is described in U.S. Pat. No. 5,780,239, which is incorporated herein by reference. Suitable sensors for heavy metals, and/or the discriminating means useful for the sensors, are described more detail in U.S. Pat. Nos. 5,595,635; 5,865,972; 5,814,205; 5,468,366, all of which are incorporated herein by reference. Suitable colorimetric calcium sensors based on Arsenazo III (acidic environment) and Cresol-phthalein Complexone (basic environment) are available from Sigma-Aldrich Chemical of St. Lois, Miss., as catalog numbers 588-3 and 587-A, respectively. Other exemplary sensors for calcium, and/or the discriminating means useful for the sensors, are described more detail in U.S. Pat. Nos. 5,705,620; 5,580,441; and 5,496,522, all of which are incorporated herein by reference.

In certain embodiments of the present invention, the sensor 40 may comprise a biosensor. As used herein, the term "biosensor" is defined as a component comprising one or more biologically reactive means being adapted to detect one or more target microorganisms or related biomolecules (e.g., an enzyme sensor, organella sensor, tissue sensor, microorganism sensor, immunosensor or electrochemical sensor), The term "biologically reactive" is defined as having the capability to selectively interact with, and preferably bind, target microorganisms and/or related biomolecules as described herein. Generally, biosensors function by providing a means of specifically binding, and therefore detecting, a target biologically active analyte. In this way, the biosensor is highly selective, even when presented with a mixture of many chemical and biological entities, such as feces. Often the target biological analyte is a minor component of a complex mixture comprising a multiplicity of biological and other components. Thus, in many biosensor applications, detection of target analytes to the parts-per-billion, parts-pertrillion, or even lower levels is necessary. Accordingly, discrimination ratios of about $10^7$–$10^8$ or greater may be required for the biosensor to recognize the target biological analyte in a complex mixture.

The biosensor of the present invention may comprise a biorecognition element, or molecular recognition element, that provides the highly specific binding or detection selectivity for a particular analyte. The biorecognition element, or system, may be a biologically derived material such as an enzyme or sequence of enzymes; an antibody; a membrane receptor protein; DNA; an organelle, a natural or synthetic cell membrane; an intact or partial viable or nonviable bacterial, plant or animal cell; or a piece of plant or mammalian tissues, and generally functions to interact specifically with a target biological analyte. The biorecognition element is responsible for the selective recognition of the analyte and the physico-chemical signal that provides the basis for the output signal.

Biosensors may include biocatalytic biosensors, and bioaffinity biosensors. In biocatalytic biosensor embodiments, the biorecognition element is "biocatalytic" and may comprise an enzyme, organelle, piece of plant or mammalian tissue, or whole cells, the selective binding sites "turn over" (i.e., can be used again during the detection process), resulting in a significant amplification of the input signal. Biocatalytic sensors such as these are generally useful for real-time, continuous sensing.

Bioaffinity sensors are generally applicable to bacteria, viruses, and toxins and include chemoreceptor-based biosensors and/or immunological sensors (i.e. immunosensors). Chemoreceptors are complex biomolecular macroassemblies responsible, in part, for a viable organism's ability to sense chemicals in its environment with high selectivity. Chemoreceptor-based biosensors comprise one or more natural or synthetic chemoreceptors associated with a means to provide a signal (visual, electrical, etc.) of the presence or concentration of a target biological analyte. In certain embodiments, the chemoreceptor may be associated with an electrode (i.e., an electrical transducer) so as to provide a detectable electrical signal. Chemoreceptors may include whole or partial nerve bundles (e.g., from antennae or other sensing organs) and/or whole or partial natural or synthetic cell membranes. On the other hand, the biorecognition elements of immunosensors are generally antibodies. Antibodies are highly specific and can be made toward bacteria, viruses, fragments of microorganisms (e.g., bacterial cell walls, parasite eggs or portions thereof, etc.), and large biomolecules. Suitable antibodies may be monoclonal or polyclonal. In any case, bioaffinity biosensors are generally irreversible because the receptor sites of the biosensor become saturated when exposed to the target biological analyte.

In certain embodiments, biocatalytic bioaffinity biosensors may be combined, such as RNA/DNA probes or other high-affinity binding systems wherein the initial biorecognition event is followed by biological amplification of the signal. For example, a specific bacteria may be detected by a bilosensor comprising genetic material, such as DNA, as a biorecognition element and PCR (i.e., polymerase chain reaction) amplification to detect small numbers (e.g., less than or equal to 500) organisms. Biocatalytic and bioaffinity biosensor systems are described in more detail in *Journal of Chromatography*, 510 (1990) 347-354 and in the *Kirk-Othmer Encyclopedia of Chemical Technology*, $4^{th}$ ed. (1992), John Wiley & Sons, NY, the disclosure of which is incorporated by reference herein.

As described above, the biosensors of the present invention preferably detect biologically active analytes common to the type of bodily waste of interest. The signal from the sensor indicating detection of a given contaminant, for example a physicochemical signal generated by the biorecognition element or elements, is preferably communicated visually to the user or caretaker (i.e., via a color change visible to the human eye). Because, as discussed above, the articles of the present invention typically have a relatively short life before disposal, it is also desirable that the signal be provided relatively rapidly, preferably within less than about 30 seconds, more preferably within less than about 15 seconds, even more preferably within less than about 10 seconds of contact between the article and the target contamination (or analyte). Other embodiments may produce optical signals, which may require other instrumentation to enhance the signal. These include flourescence, bioluminesence, total internal reflectance resonance, surface plasmon resonance, Raman methods and other laser-based methods. For example, exemplary surface plasmon resonance biosensors are available as IBIS I and IBIS II from XanTec Analysensysteme of Muenster, Germany, which may comprise bioconjugate surfaces as biorecognition elements. Alternatively, the signal may be processed via an associated transducer, as described previously and further below. The signal may be qualitative (e.g., indicating the presence of the target biological analyte) or quantitative (i.e., a measurement of the amount or concentration of the target biological analyte). In such embodiments, the transducer may optionally produce an optical, thermal or acoustic signal. The signal may also be durable or transient, and the sensor may be adapted to detect and/or signal only concentrations of the contamination above a predefined threshold level, as described previously.

As a non-limiting example, ABTECH, Scientific, Inc., of Yardley, Penn. offers "bioanalytical biotransducers", available as BB Au-1050.5-FD-X, which may be rendered biospecific (for microorganisms or other target biological analytes as described herein) by covalently immobilizing polypeptides, enzymes, antibodies, or DNA fragments to their surfaces. Other suitable microbial biosensors are described in U.S. Pat. No. 5,869,272 (gram negative organisms); U.S. Pat. Nos. 5,830,341; 5,795,453; 5,354,661; 5,783,399; 5,840,488; 5,827,651; 5,723,330; and 5,496,700, all of which are incorporated herein by reference.

The biosensors of the present invention may also comprise biorecognition systems, including enzymes or binding proteins such as antibodies immobilized onto the surface of physico-chemical transducers. For example, a specific strain of bacteria may be detected via biosensors employing antibodies raised against that bacterial strain. Alternatively, a target bacteria may be detected by a biorecognition element (including antibodies and synthetic or natural molecular receptors) specific to extracellular products of the target bacteria, such as toxins produced by that strain (e.g., *E. coli*). Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively. Both of these patents are incorporated by reference herein.

In any of the foregoing examples, the specific microorganism may be directly detected or may be detected by binding a toxin, enzyme, or other protein produced by the organism or an antibody, such as a monoclonal antibody, specific to the organism. Exemplary biosensors adapted to detect proteolytic enzymes are described in U.S. Pat. No. 5,607,567 and toxins in U.S. Pat. Nos. 5,496,452; 5,521,101; and 5,567,301.

In biosensor embodiments wherein the biorecognition element does not produce signal which is easily discerned by a user of the article in which the sensor is employed (e.g., color change), the sensor 40 may include a transducer in communication with the biorecognition element in order to corIvert the physico chemical signal from the biorecognition element into a usable signal to the wearer, caretaker, or component of the article (e.g., an actuator). Exemplary transducers may include electrochemical transducers (including potentiometric, amperometric, and conductimetric transducers), optical transducers (including flourescence, bioluminesence, total internal reflective resonance, and surface plasmon resonance), thermal transducers, and acoustic transducers, as known in the art. A power source, such as a miniature 3 volt watch battery or printed thin film lithium battery, may be connected with the sensor 40 to provide any required power.

The effectiveness of the biosensors of the present invention may be measured with the Response Factor Test described in the Test Method section below. The Response Factor describes the ratio of the response of the biosensor when exposed to fecal test material compared to the response of the biosensor when exposed to physiological saline solution and is useful in assessing the sensitivity of the biosensor for biologically active analytes expected to be found preferentially in feces versus urine. The biosensors of the present invention preferably have a response factor of at least 2, 3, or 5, more preferably at least 10, and even more preferably at least 20 when exposed to fecal test material in aqueous solution or test urine having a concentration of 1 gram of fecal test material per 1 gram of physiological saline solution. (Physiological saline solution is used here to represent the background input signal which is present in most natural environments such as aqueous body fluids.) Such biosensors are able to clearly distinguish between the presence of fecal material and the presence of physiological saline solution with respect to a target biologically active analyte specific to feces.

One way to detect feces is to detect skatole, a substance commonly found in fecal material. It has been found that the skatole concentration in feces is about 180 microgram per gram of fecal material whereas the skatole level in urine has been found to be substantially lower. Skatole is generally a product of microbiological degradation that originates from the catabolism of tryptophane in the intestinal system. In one preferred embodiment of a skatole detecting biosensor, the biosensor comprises genetically engineered microorganisms which assimilate skatole and or other substances. The assimilation of skatole specific substances can be measured, for example, via the oxygen consumption during the assimilation process. Microorganisms suitable for detecting skatole include *Acinetobacter baumannii* TOI36 (FERM P-12891, Japanese patent publication JP05304947), and *Bacillus sp* TOI41(FREM P-12914, disclosed in Japanese patent publication JP05304948). Suitable biosensors including such microorganisms are commercially available for example from Institut für Chemo- und Biosensorik of Münster, Germany, under the designation Mikrobielle Sensoren.

If microorganisms are incorporated into a biosensor, they may be immobilized in the biosensor by techniques known in the art such as entrapment, adsorption, crosslinking, encapsulation, covalent attachment, any combination thereof, or the like. Further, the immobilization can be carried out on or within many different substrates such as known the art. In certain preferred embodiments, the immobilization substrate may be selected from the group of polymer based materials, hydrogels, tissues, nonwoven materials, woven materials.

Surface wipe articles which perform an efficacious waste contamination "cleaning" (for example, removal) function, in addition to the waste contamination detection and signaling functions described above, are one preferred embodiment of the present invention. As used herein "efficacious" cleaning means that the article is capable of substantially, if not entirely, removing or otherwise mitigating the target waste contamination from the surface of interest. Surface wipe articles which can perform such a waste contamination cleaning function include cleaning articles such as facial tissues, is toilet tissues, paper towels, wet or dry wipes and the like. Both wet and dry cleaning devices and articles are included, the former of which are suitable for cleaning objects without need for aqueous cleaning liquids, or if they do use aqueous cleaning liquids relatively small amounts are used. Surface wipe articles of this embodiment can comprise the wet (for example, premoistened) or dry substrates, and a waste contamination sensor, as described previously and as shown in FIG. 1. As is apparent, by performing a waste removal function, such surface wipe.articles can advantageously be used to decontaminate a contaminated surface after contamination is detected and signaled to a user of the article.

Figure 2A:
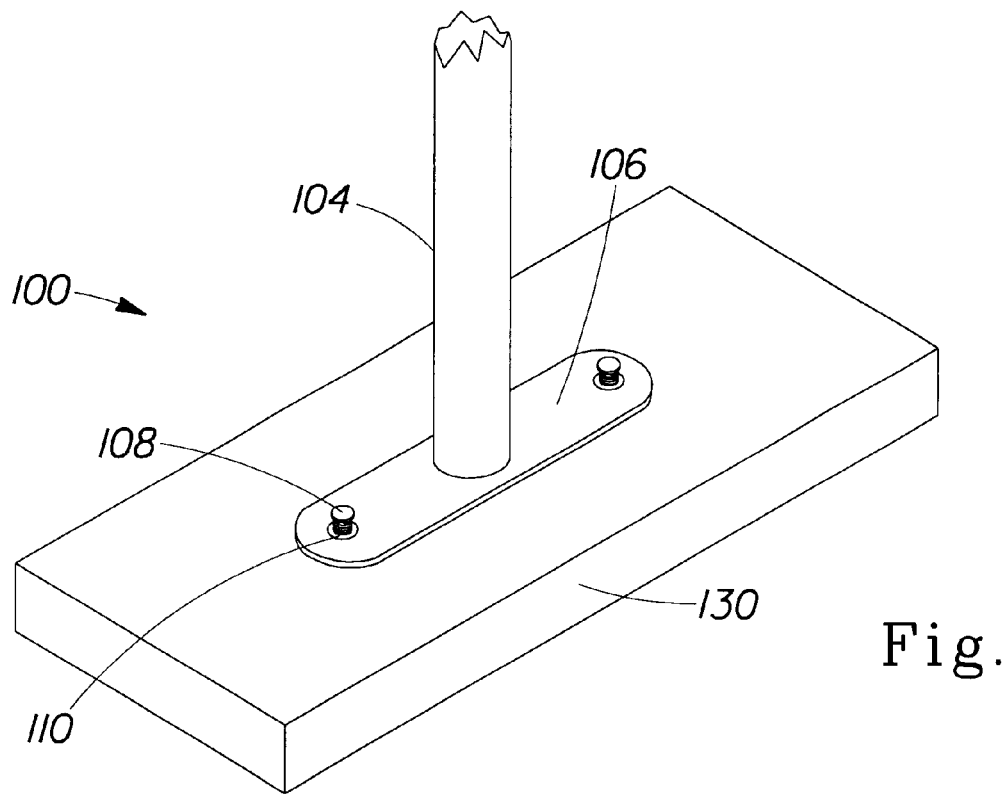
FIG. 2 is a perspective view of the lower portion of a mop with a disposable mop head comprising a disposable surface wipe article of the invention.
Figure 2B:
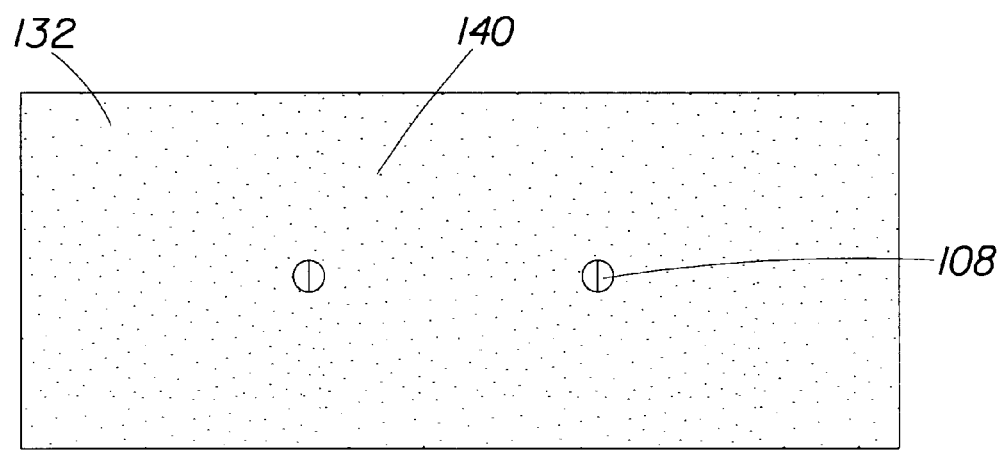

In another preferred embodiment, such as exemplified in FIGS. 2A and 2B, a disposable mop 100 having a waste contamination sensor of the invention is shown. The mop 100 comprises an elongated handle 104 and a mop head substrate 130 connected to one end of the elongated handle 104 via a bracket 106. In this embodiment the mop head substrate 130 is disposable, and substrate 130 can be made of a material or materials (ideally biodegradable) preferably suitable for performing a waste contamination removal function. Suitable substrates are described below and previously herein. Bracket 106 has threaded orifices 110 through which screws 108 extending upward through mop head substrate 130, thereby securing the mop head substrate to the bracket. The elongated handle 104 can be connected to the bracket 106 by any suitable means as will be known in the art, such as by screwing into the bracket, nails, staples, glue, etc. Referring to FIG. 2B, shown is the bottom surface 132 of the mop head substrate 130, which is the portion of the mop head which would typically contact the surface to be treated during normal use. Waste contamination sensor 140, such as a sensor described previously herein, is incorporated into or onto at least part of the bottom surface 132 of substrate 130. Screws 108 extend from the mop head substrate 130 upward toward the bracket 106 where they are affixed in place by threaded orifices 110. Preferably screws 108 are recessed into the mop head substrate 130 so they do not contact the surface to be wiped with the mop.

Figure 3A:
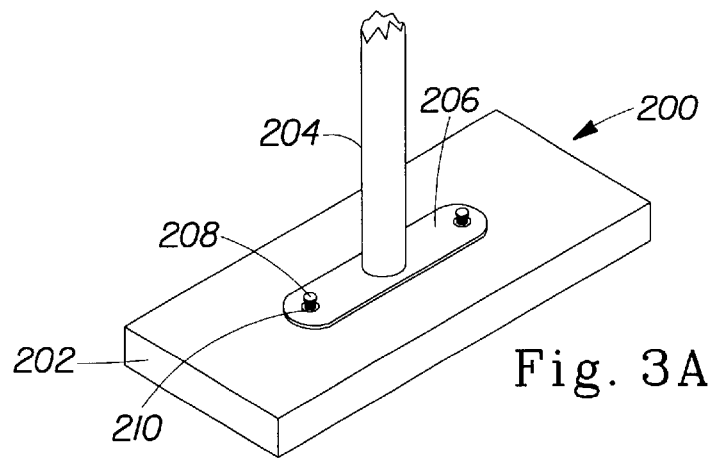
FIG. 3 is a perspective view of the lower portion of a mop with a disposable mop head cover comprising a comprising a disposable surface wipe article of the invention.
Figure 3B:
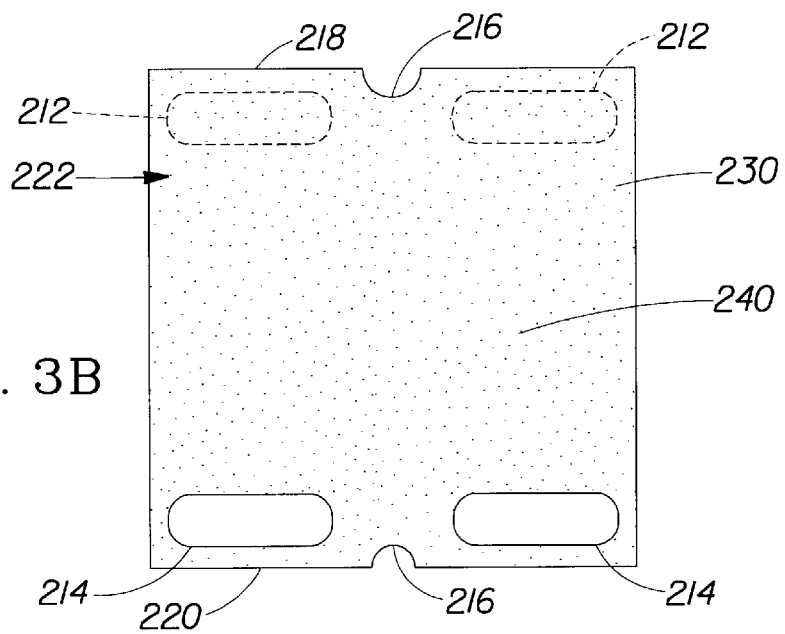
Figure 3C:
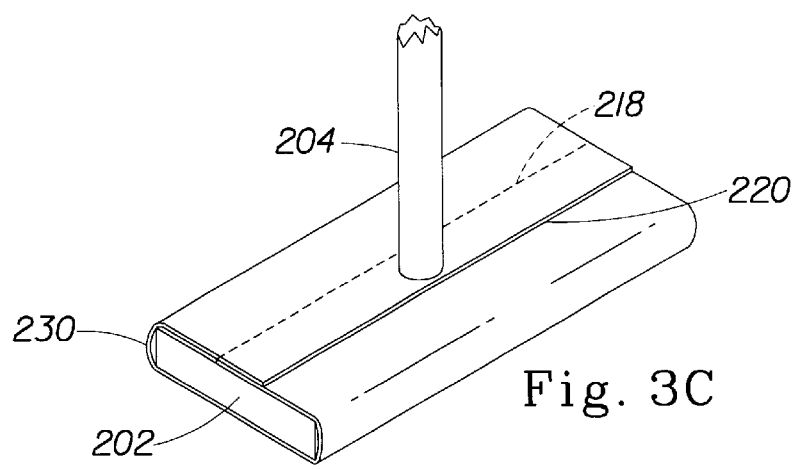

FIGS. 3A, 3B and 3C show another disposable mop embodiment. Mop 200 includes a disposable mop head cover substrate 230 which a fits mop head 202. Mop head cover substrate 230 has a first edge 218, second edge 220, and outward face 222. Substrate 220 can be made of a material or materials (ideally biodegradable), preferably suitable for performing a waste contamination removal function, and suitable are described below and previously herein. As shown in FIG. 3C, mop head cover substrate 230 wraps around mop head 202 with first edge 218 overlapping second edge 220 and is held in place by the hook portion of hook and loop fasteners 212, located near the first edge 218 on the opposite face of the substrate from the outer face 222, and loop portion of hook and loop fasteners 214, located near the second edge 220 on the outer face 222. Handle orifices 216 facilitate good fit around the handle 204. Waste contamination sensor 240, such as a sensor as described previously herein, is incorporated into or onto at least part of outward face 222 of substrate 230.

Substrates which are suitable for use with the present invention, and especially for cleaning devices such as a dry mop, are more fully described in U.S. patent application Ser. No. 09/082,349 entitled "Novel Structures Useful As Cleaning Sheets", filed May 20, 1998; and U.S. patent application Ser. No. 09/082,396 entitled "Novel Three Dimensional Structures Useful As Cleaning Sheets", filed May 20, 1998, both of which are hereby incorporated herein by reference. While the above-described sheets are preferred, it will be understood that other substrates, including non-fibrous substrates such as a closed cell or open cell foam, described above may be equally suitable for use with the present invention.

Figure 4:
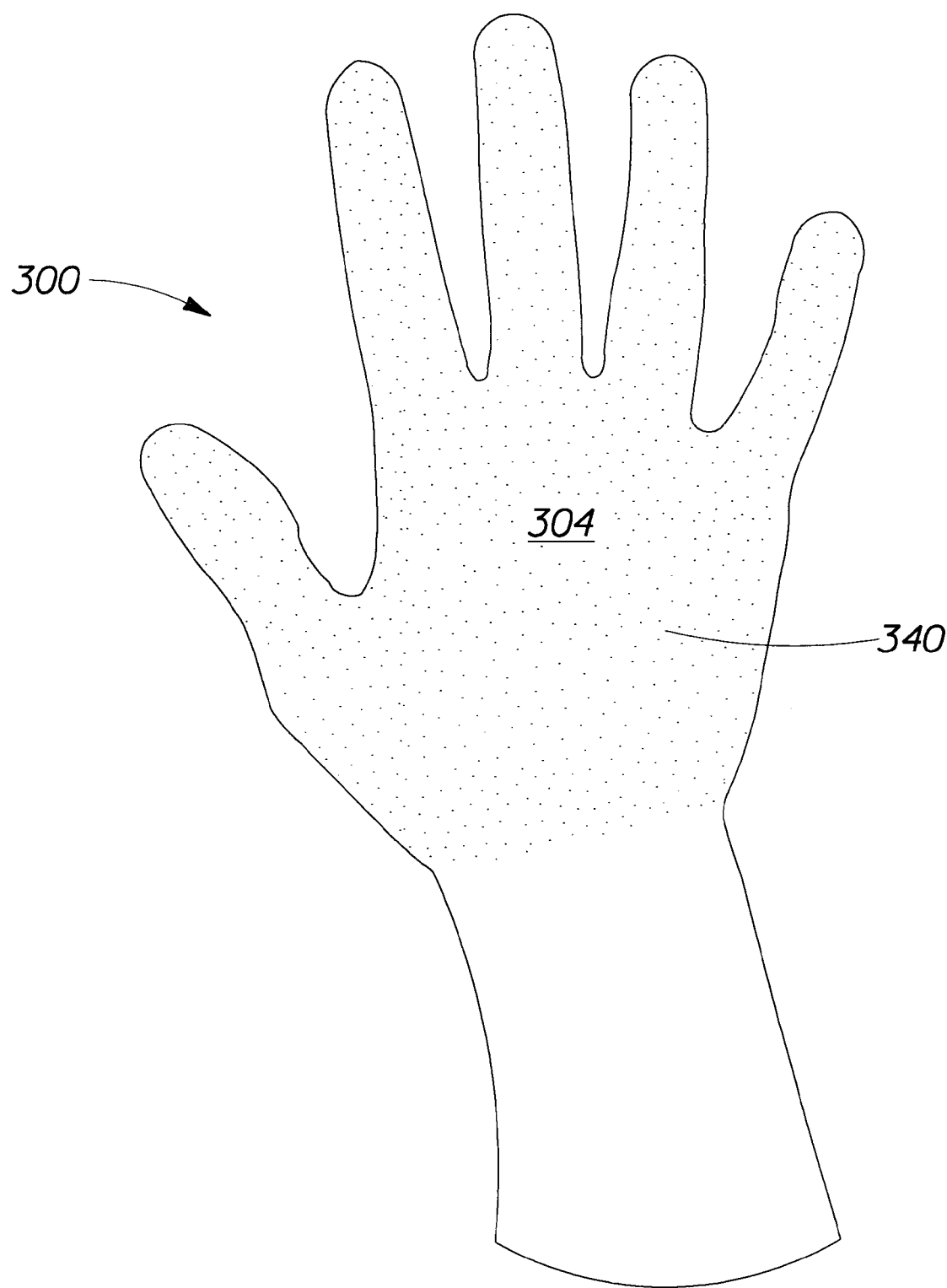
FIG. 4 is a perspective view of a surface wipe article of the invention in the form of a glove, shown palm-side up.

As shown in FIG. 4, in an alternative embodiment, the present invention may comprise a surface wipe article in the form of a hand covering 300 which can detect and alert the user to specific waste contamination conditions. The hand cover can partially or wholly cover the hand. Preferably, a sensor 340 is generally located on at least a portion of an exterior palm-side surface 304 of hand covering 300. Example forms of handcovers include but are not limited to finger cots, gloves, mittens and hand wraps. Preferably, such body coverings are disposable. Such coverings may be used, for example, by caregivers for babies or incontinent individuals, in a medical care environment, and so forth.

Figure 5:
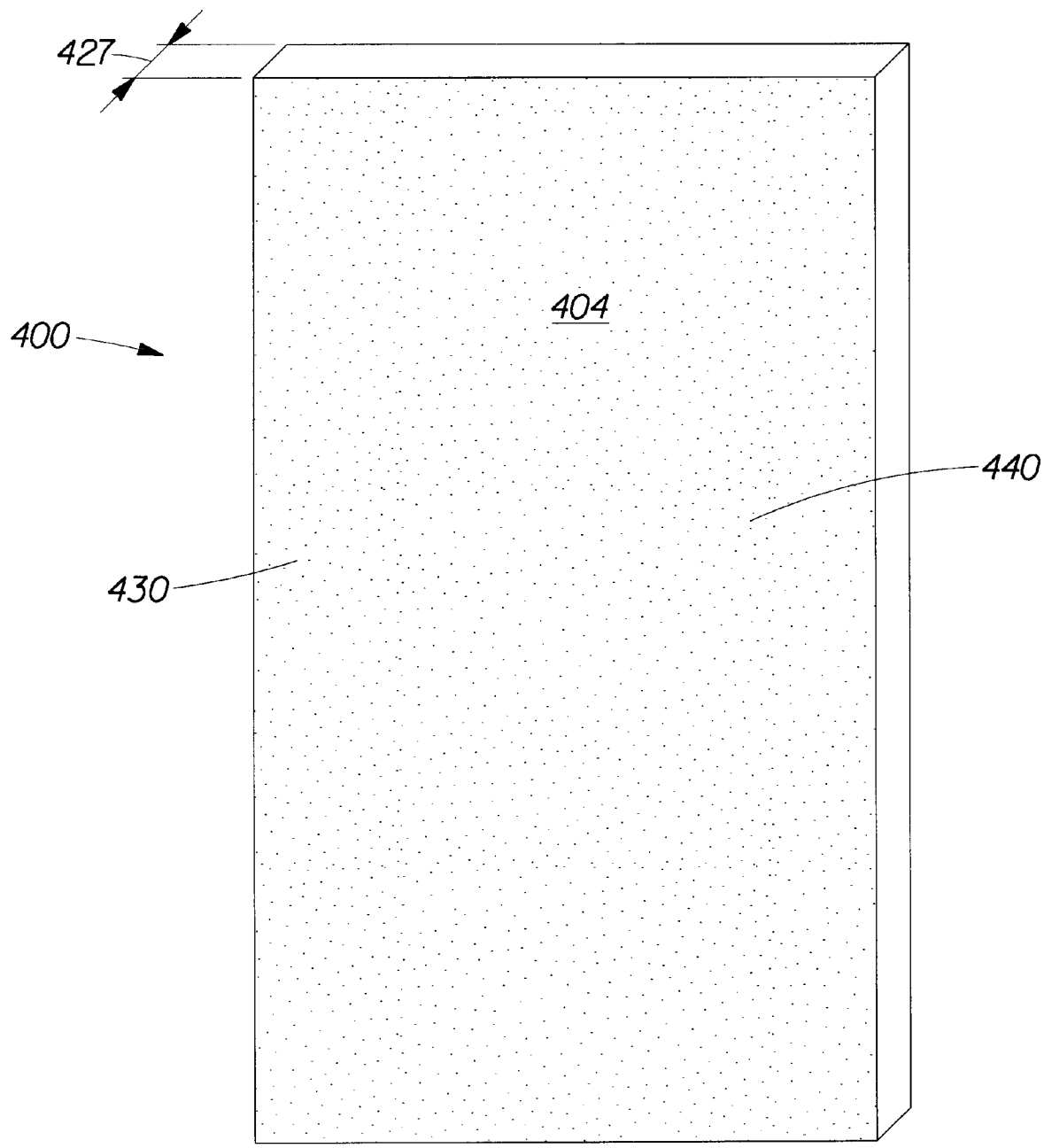
FIG. 5 is a perspective view of an alternative embodiment of the invention, in the form of a disposable changing table pad.

The present invention can also be employed in connection with disposable covers for surfaces including disposable bibs, disposable baby diaper changing pads or "mats", disposable bed pads, and disposable cutting surfaces, among others, which may become contaminated with bodily waste incidental to their primary uses. FIG. 5 shows a disposable baby diaper changing pad 400 including a substrate 430 having a thickness 427. Substrate 430 has an upper surface 404 which would typically be in contact with a baby while the baby's diaper is being changed. Substrate 430 can be made from a dry fibrous woven or nonwoven material to provide a clothlike feel to surface 404, or from a close celled or open celled foam for cushioning, or a combination of such materials preferably with surface 404 formed from the fibrous material for the foregoing reason. Other substrates, described above may be equally suitable for use with these embodiments of the present invention. Waste contamination sensor 440, such as a sensor as described previously herein, is incorporated into or onto at least part of surface 404 of substrate 430.

Test Method

Response Factor Test:

With the Response Factor Test: as described hereafter the response of a quantitative sensor as a reaction to exposure to a specific substance or composition can be measured.

The specific substances or compositions for which this test is suitable are: fecal test material in aqueous solution having a concentration of 1 gram of fecal test material per 1 gram of physiological saline solution; fecal test material in test urine solution having a concentration of 1 gram of fecal material per 1 gram of test urine solution; test urine solution; and a solution of skatole in physiological saline solution having a concentration of 180 micrograms of skatole per gram of physiological saline solution; and physiological saline solution.

All measurements are taken at body temperature (37° Celsius). The method includes the following steps in the following order:

1) Record quantitative response of sensor after exposition to physiological saline solution for 24 hours. The background response is the maximum recorded response.
2) Expose sensor to specified substance or composition.
3) Record quantitative response of sensor while sensor is still exposed to the specified substance or composition for 24 hours. Substance response is the maximum recorded response.

The Response Factor is obtained by normalizing the substance response with the background response. In case, the thus obtained Response Factor is less than 1, the reciprocal value of the Response Factor is reported as the Response Factor.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. It is therefore intended to cover in the appended claims all such changes and modifications that are within the scope of this invention.

What is claimed is:

1. A disposable surface wipe article comprising:

a sensor comprising a biosensor having at least one immunosensor, the sensor being adapted to detect bodily waste contamination on a surface contacted by the article and to provide a signal to a user of the article indicating the presence of the waste contamination on the surface and wherein the signal is provided within less than about 30 seconds from the time the article contacts the bodily waste on the surface.

2. The article of claim 1, wherein the article is a cleaning article.

3. The article of claim 2, wherein the cleaning article is selected from the group consisting of a baby wipe, a hand wipe, a paper towel, a toilet tissue, and a facial tissue.

4. The article of claim 3 wherein the cleaning article is a wet wipe or a dry wipe.

5. The article of claim 1 wherein the sensor is adapted to detect a component of said bodily waste normally present in bodily waste excreted by healthy individuals.

6. The article of claim 1 wherein the sensor is adapted to detect a component of bodily waste selected from the group consisting of feces, urine, mucous, sebum, saliva, sweat, ejaculates, and menses.

7. The article of claim 6, wherein the sensor is adapted to detect alkaline phosphatase.

8. The article of claim 1 wherein the signal is visible to the unaided human eye.

9. The article of claim 8 wherein the signal is a colorimetric signal.

10. The disposable article of claim 1 wherein the signal is durable throughout at least the useful life of the article.

11. The article of claim 1, wherein the article further comprises a substrate which incorporates the sensor.

12. The article of claim 11, wherein the substrate comprises a fibrous web.

13. The article of claim 11 wherein the sensor is associated with a carrier structure attached to the substrate.

14. The article of claim 1 wherein the surface is an animate surface or an inanimate surface.

15. A disposable surface wipe article comprising:

a sensor comprising a biosensor having at least one immunosensor;

the sensor being adapted to detect bodily waste contamination on a surface contacted by the article and to provide a signal to a user of the article indicating the presence of the waste contamination on the surface wherein the surface is human skin.

16. A disposable surface wipe article comprising:

a sensor comprising a biosensor having at least one immunosensor;

the sensor being adapted to detect bodily waste contamination on a surface contacted by the article and to provide a signal to a user of the article indicating the presence of the waste contamination on the surface, wherein the article further comprises an element to control access to the sensor and the element to control is selected from the group consisting of a semipermeable membrane, a coating, and a water-soluble coating.

17. A disposable surface wipe article comprising:

a substrate containing aqueous fluid;

a sensor comprising a biosensor having at least one immunosensor;

the sensor being adapted to detect one or more of an abnormal health marker or an abnormal nutritional marker present in excreted bodily waste present on a surface capable of being wiped by the article, and to signal the presence of the abnormality to a user of the article, wherein the signal is provided within less than about 30 seconds from the time the article contacts the bodily waste on the surface.

18. The article of claim 17 wherein the sensor is adapted to detect one or more of a health marker or a nutritional marker in bodily waste selected from the group consisting of feces, urine, mucous, saliva, sebum, sweat, ejaculates, and menses.

19. The article of claim 17 wherein the signal is visible to the unaided human eye.

20. The article of claim 19 wherein the signal is a calorimetric signal.

21. The article of claim 20 wherein the signal is provided within less than about 10 seconds from the time the article contacts the bodily waste containing the marker.

22. A disposable surface covering article comprising:

a sensor comprising a biosensor having at least one immunosensor;

the sensor being adapted to detect bodily waste contamination of the article and to provide a signal to a user of the article indicating the presence of the waste contamination, wherein the signal is durable throughout at least the useful life of the article.

23. The article of claim 22 wherein the sensor is adapted to detect a component of said bodily waste normally present in bodily waste excreted by healthy individuals.

24. The article of claim 22 wherein the sensor is adapted to detect a component of bodily waste selected from the group consisting of feces, urine, mucous, saliva, sebum, sweat, ejaculates and menses.

25. The article of claim 22 wherein the signal is visible to the unaided human eye.

26. The article of claim 22, wherein the article further comprises a substrate which incorporates the sensor.

* * * * *

UNITED STATES PATENT AND TRADEMARK OFFICE
CERTIFICATE OF CORRECTION

PATENT NO.    : 6,501,002 B1
DATED         : December 31, 2002
INVENTOR(S)   : Donald C. Roe et al.

It is certified that error appears in the above-identified patent and that said Letters Patent is hereby corrected as shown below:

Column 2,
Line 35, delete "nonfibrous" and insert -- non-fibrous --.

Column 4,
Line 55, delete "lipdphilic" and insert -- lipophilic --.

Column 5,
Line 3, delete "consisting," and insert -- consisting --.
Line 39, delete "comeum" and insert -- corneum --.

Column 7,
Line 7, delete "faces" and insert -- feces --.
Line 19, delete "the," and insert -- the --.

Column 8,
Line 37, delete "the," and insert -- the --.

Column 9,
Line 11, delete "the;" and insert -- the --.
Line 42, delete "contamination.," and insert -- contamination. --.

Column 10,
Line 8, delete "(wNV)." and insert -- (w/V). --.
Line 50, delete ":better" and insert -- better --.

Column 11,
Line 17, delete "St. Lois," and insert -- St. Louis --.
Line 41, delete "pertrillion," and insert -- per-trillion --.
Line 62, delete "of.plant" and insert -- of plant --.

Column 12,
Line 44, delete "physicochemical" and insert -- physico-chemical --.

Column 13,
Line 51, delete "corIvert" and insert -- convert --.

Column 14,
Line 12, delete "fluids.)" and insert -- fluids). --.
Lines 35-36, delete "Müinster," and insert -- Münster, --.
Line 67, delete "wipe.articles" and insert -- wipe articles --.

UNITED STATES PATENT AND TRADEMARK OFFICE
CERTIFICATE OF CORRECTION

PATENT NO. : 6,501,002 B1
DATED : December 31, 2002
INVENTOR(S) : Donald C. Roe et al.

It is certified that error appears in the above-identified patent and that said Letters Patent is hereby corrected as shown below:

Column 16,
Line 31, delete "Test:" and insert -- Test --.

Column 17,
Line 7, delete "immunosensor," and insert -- immunosensor; --.
Line 35, between Claim 9 & Claim 10, insert the following:
-- 10. The article of claim 1 wherein the signal is provided within less than about 15 seconds from the time the article contacts the bodily waste on the surface.
11. The article of claim 1 wherein the signal is provided within less than about 10 seconds from the time the article contacts the bodily waste on the surface.
12. The article of claim 1 wherein the signal is provided within less than about 5 seconds from the time the article contacts the bodily waste on the surface. --.
(Please renumber the remaining claims and their dependencies).

Column 18,
Line 31, delete "calorimetric" and insert -- colorimetric --.

Signed and Sealed this

Eleventh Day of April, 2006

JON W. DUDAS
*Director of the United States Patent and Trademark Office*